(12) United States Patent
Rocke et al.

(10) Patent No.: US 9,037,255 B2
(45) Date of Patent: May 19, 2015

(54) DEVICE FOR CONTROLLING THE ELECTRIC CHARGE ON STIMULATING ELECTRODES

(75) Inventors: Andre Rocke, Garbsen (DE); Maurits Ortmanns, Ulm (DE); Norbert Unger, Braunschweig (DE)

(73) Assignee: PIXIUM VISION SA (FR)

( * ) Notice: Subject to any disclaimer, the term of this patent is extended or adjusted under 35 U.S.C. 154(b) by 1457 days.

(21) Appl. No.: 11/721,530

(22) PCT Filed: Dec. 9, 2005

(86) PCT No.: PCT/EP2005/013258
§ 371 (c)(1),
(2), (4) Date: Aug. 20, 2009

(87) PCT Pub. No.: WO2006/063743
PCT Pub. Date: Jun. 22, 2006

(65) Prior Publication Data
US 2010/0070005 A1    Mar. 18, 2010

(30) Foreign Application Priority Data

Dec. 13, 2004    (DE) .......................... 10 2004 059 973

(51) Int. Cl.
*A61N 1/00*      (2006.01)
*A61N 1/08*      (2006.01)
*A61N 1/36*      (2006.01)

(52) U.S. Cl.
CPC .............. *A61N 1/08* (2013.01); *A61N 1/36046* (2013.01)

(58) Field of Classification Search
CPC ... A61N 1/08; A61N 1/36139; A61N 1/3615; A61N 1/3616; A61N 1/36153; A61N 1/36157; A61N 1/3782

USPC ...................................................... 607/62, 57
See application file for complete search history.

(56) References Cited

U.S. PATENT DOCUMENTS 5,376,104 A    12/1994    Sakai et al.
5,486,201 A    1/1996     Canfield
(Continued)

FOREIGN PATENT DOCUMENTS

| CA | 2010988  | 9/1990 |
|----|----------|--------|
| CA | 2475294  | 8/2003 |
| DE | 10151650 | 5/2003 |

OTHER PUBLICATIONS

International Search Report for PCT/EP2005/013258, date of mailing Mar. 3, 2006, 2 pages.
(Continued)

*Primary Examiner* — Niketa Patel
*Assistant Examiner* — William Levicky
(74) *Attorney, Agent, or Firm* — Workman Nydegger

(57) ABSTRACT

A device for stimulating living tissue or nerves by individual or repeated stimulating pulses via stimulating electrodes which stimulate living tissue or nerves by stimulating pulses includes an electrical circuit which regulates the electric voltage or charge on the stimulating electrodes as a function of the electric voltage between the stimulating electrodes and reduces or equalises imbalances of electric charges on the stimulating electrodes. This device is capable of equalizing the electric charge on the stimulating electrodes of a stimulation system. The device and the process for using the device have the advantage that imbalances of electric charges on the stimulating electrodes, and the associated disadvantageous effects on the tissue and on the nerves, are avoided or eliminated. Furthermore, the device has a small space requirement.

21 Claims, 3 Drawing Sheets

(56) References Cited

U.S. PATENT DOCUMENTS

| | | | |
|---|---|---|---|
| 5,672,464 A | 9/1997 | Nelson | |
| 5,899,923 A * | 5/1999 | Kroll et al. | 607/5 |
| 6,301,505 B1 | 10/2001 | Money | |
| 6,473,649 B1 * | 10/2002 | Gryzwa et al. | 607/28 |
| 6,826,430 B2 * | 11/2004 | Faltys et al. | 607/137 |
| 7,809,437 B2 * | 10/2010 | Palmer et al. | 607/2 |
| 2002/0169486 A1 * | 11/2002 | Chow et al. | 607/54 |
| 2006/0224199 A1 * | 10/2006 | Zeijlemaker | 607/11 |

OTHER PUBLICATIONS

Written Opinion of the International Searching Authority for PCT/EP2005/013258, date of mailing Jun. 21, 2007, 5 pages.

* cited by examiner

DEVICE FOR CONTROLLING THE ELECTRIC CHARGE ON STIMULATING ELECTRODES

CROSS REFERENCE TO RELATED APPLICATIONS

The present Application claims the benefit of priority to the following International Application: PCT/EP2005/013258 titled "Device for Controlling the Electric Charge on Stimulating Electrodes" filed on Dec. 9, 2005, which claims priority to German Patent Application No. DE 102004059973.4 filed on Dec. 13, 2004 (which are both incorporated by reference in their entirety).

FIELD

The present invention relates to a device for controlling the electric voltage or the electric charge on stimulating electrodes that serve for the stimulation of living tissue or nerves. The present invention relates, in particular, to an electronic circuit for controlling the electric charge on stimulating electrodes in a system for stimulating living tissue or nerves by individual or repeated stimulating pulses via stimulating electrodes.

BACKGROUND

Devices in the form of implants for stimulating living tissue are already known. For instance, implants for the retina of the human eye have been developed that are provided for the purpose of treating patients whose eyesight has been partially or completely lost as a result of defects in the retina. In this case, in principle a microelectronic device having a plurality of light-sensitive pixel elements is implanted in the region of the retina, via which an image projected onto the retina by the still-intact lens of the eye is registered; alternatively, the registration of the image may also be effected by means of an external camera. The image registered by the pixel elements or by the camera is converted into electrical signals and output to the surrounding tissue—or, to be more exact, to the cells of the retina—via stimulating electrodes by means of electrical stimulating pulses, in order in this way to restore or to improve the eyesight of the patient who has lost, or partially lost, his or her sight.

Imbalances of electric charges on the stimulating electrodes may arise in the course of the stimulation of living tissue or nerves by individual or repeated stimulating pulses via stimulating electrodes. In known stimulation systems or stimulators, use is frequently made of pulse-generators, in order to generate the electrical stimulating pulses at the stimulating electrodes. In this case the shape or contour of the electrical stimulating pulses is adapted to the type of tissue to be stimulated. Via a current-generator the stimulating electrodes have electric current applied to them that corresponds to the electrical stimulating pulses generated by the pulse-generator.

However, after an individual stimulating pulse a small electric charge may be left behind on the stimulating electrode, for example by reason of errors or tolerances. A continuously residual or increasing imbalance of the electric charges on the stimulating electrodes may result in an undesirable flow of current between the stimulating electrodes, and hence in damage both to the tissue and to the stimulating electrodes, which may lead to the destruction of the stimulating electrodes and to the total failure of the stimulation system. By reason of imbalances of electric charges on the stimulating electrodes, in particular a flow of direct current may occur between the stimulating electrodes, which for the patient may be associated with unpleasant sensations and disadvantageous effects on the tissue or on the nerves.

In some known stimulation systems the elimination of imbalances of electric charges on the stimulating electrodes is effected, for example, by short-circuiting the electrodes or by means of parallel resistors for passive discharging of the stimulating electrodes or of series capacitors which are customarily used. However, such devices have the disadvantage that they are associated with a large space requirement, for it is desirable, in principle, to accommodate stimulation systems in as small a space as possible.

U.S. Pat. No. 6,301,505 B1 describes a device for stimulating nerve tissue, in particular in the inner ear or pertaining to muscle tissue. An electrical circuit monitors the build-up of potential between the stimulating electrodes. As soon as a potential between the stimulating electrodes is detected that is too high, further stimulations are prevented, so that the potential difference between the stimulating electrodes is unable to build up further. A stimulation of the stimulating electrodes is then suppressed until such time as, by virtue of a short circuit between the electrodes, the potential difference has been equalised again or lies below the limiting value. This device has the disadvantage that no stimulation can be performed until a potential difference between the stimulating electrodes has been equalised.

DE 101 51 650 A1 describes an electrode arrangement for electrical stimulation with a stimulating electrode, via which a stimulus signal is supplied to biological material, and with a counter-electrode. In addition, the electrode arrangement is equipped with a sensor electrode, with which a polarising voltage on the stimulating electrode is determined, as a result of which static portions of the electrode polarisation can also be detected. According to this known process, the polarising potential is measured continuously, and the stimulating signal is influenced in such a manner that the polarising potential between the stimulating electrodes does not exceed a defined value. This is obtained either by adjusting the amplitude or by switching the stimulating signal off. The disadvantage of this electrode arrangement consists in the fact that with the sensor electrode an additional electrode is needed for measuring the polarising potential, which increases the costs of the stimulation device, the effort in connection with the implantation, and the damage to the tissue to be stimulated. Furthermore, with this known method the measurement of a potential difference between the stimulating electrodes is effected during the stimulation, as a result of which the result of measurement may be impaired.

The object underlying the present invention is to create a device having little space requirement for the purpose of controlling the electric charge on stimulating electrodes, said device reducing or eliminating an undesirable flow of current between the stimulating electrodes of a stimulation system by reason of imbalances of electric charges on the stimulating electrodes.

This object is achieved by means of the device according to the invention with the features according to Claim 1 and also by means of a process with the features according to Claim 14. Advantageous further developments of the invention are specified in each of the dependent claims.

SUMMARY

According to one aspect of the present invention, the aforementioned object is achieved by means of a device for stimulating living tissue or nerves by individual or repeated stimulating pulses via stimulating electrodes which are contacted with living nerves or tissue that are/is stimulated by the stimulating pulses of the stimulating electrodes, said device comprising an electrical circuit which controls the electric voltage or the electric charge on the stimulating electrodes as a function of the electric voltage between the stimulating electrodes and reduces or equalises imbalances of electric charges on the stimulating electrodes.

According to a further aspect of the present invention, the aforementioned object is achieved by means of a process for operating the aforementioned device comprising the following steps: ascertaining an electric voltage between the stimulating electrodes or ascertaining an imbalance of electric charges on the stimulating electrodes, comparing the ascertained voltage between the stimulating electrodes with a predetermined voltage range, and generating and applying a positive or negative electric current of defined duration and intensity to at least one stimulating electrode, as a result of which the electric voltage between the stimulating electrodes, or an imbalance of electric charges on the stimulating electrodes, is reduced or equalised.

According to the present invention, a device, and also a process for operating the device, is consequently made available that is capable of regulating the electric charge on stimulating electrodes of a system for stimulating living tissue or nerves, and of bringing about an equalisation of charge on the stimulating electrodes. The present invention makes available, in particular, an electronic circuit that serves for controlling and equalising the electric charge on stimulating electrodes in a system for stimulating living tissue or nerves by individual or repeated stimulating pulses via stimulating electrodes. The device according to the invention is therefore capable of bringing about an equalisation of the electric charge on the stimulating electrodes of the stimulation system.

A particular advantage of the device according to the invention consequently consists in the fact that imbalances of electric charges on the stimulating electrodes and the associated disadvantageous effects on the tissue and on the nerves are avoided, in that they are actively eliminated by an appropriate charge equalisation. A further advantage of the device according to the invention consists in the fact that it no longer requires use of series capacitors, and therefore has a smaller space requirement than known devices. Although the use of at least one parallel resistor is not absolutely essential, it may be provided, where appropriate, for the purpose of enhancing the initial-error security. Yet another advantage of the device according to the invention consists in the fact that, besides the stimulating electrodes, no additional measuring electrode is needed.

BRIEF DESCRIPTION OF THE FIGURES

Further particulars, preferred embodiments and advantages of the present invention will become apparent from the following description with reference to the drawing.

DETAILED DESCRIPTION

Figure 1:
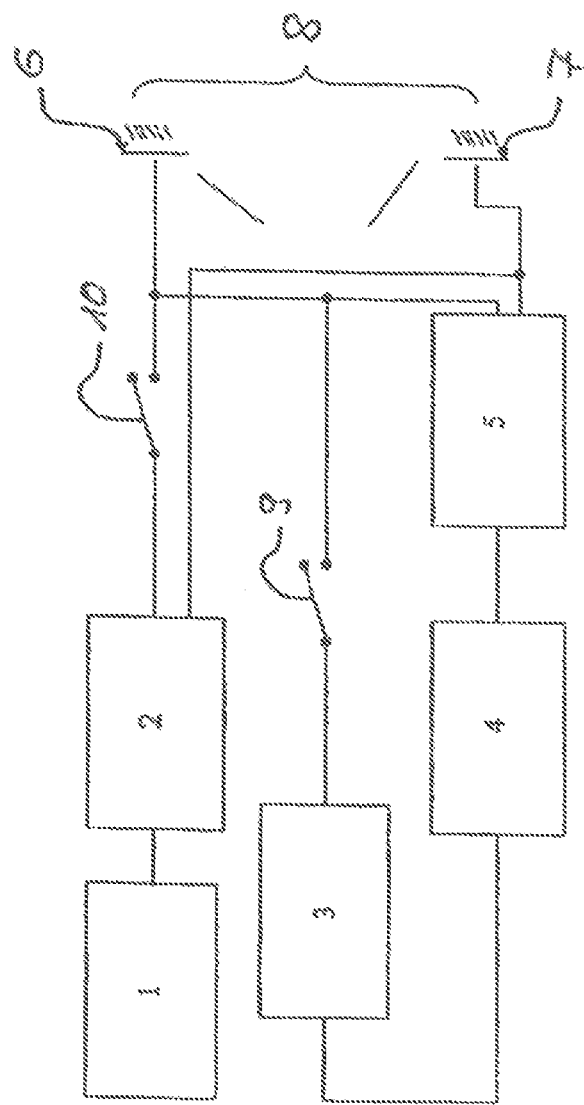
FIG. 1 shows a schematic block diagram of an electrical circuit for a device according to a preferred embodiment of the present invention for use in a stimulation system.

Represented in FIG. 1 is a schematic block diagram of an electrical circuit for a device according to a first preferred embodiment of the present invention which can be employed in a stimulation system for stimulating living tissue or nerves by individual or repeated stimulating pulses. In this preferred embodiment of the present invention, the device according to the invention includes a pulse-generator 1 which generates electrical pulses. These electrical pulses are passed from the pulse-generator 1 to a current/voltage source 2, where they are amplified into stimulating pulses and transmitted by electrical lines to a first stimulating electrode 6 and to a second stimulating electrode or counter-electrode 7.

The stimulating electrodes 6, 7 are, for example, contacted with human nerves or tissue 8 that are/is stimulated by the stimulating pulses of the stimulating electrodes 6, 7. In this case the shape or contour of the electrical stimulating pulses generated by the pulse-generator 1 and by the current/voltage source 2 is adapted to the type of tissue to be stimulated or to the type of nerves to be stimulated. The connection via the electrical line between the current/voltage source 2 and the stimulating electrode 6 can be interrupted or established by a switching contact 10.

The embodiment of the device according to the invention represented in FIG. 1 for stimulating living tissue or nerves further includes a coulombmeter or voltmeter 5 which is connected to the two stimulating electrodes 6 and 7. The coulombmeter or voltmeter 5 ascertains the electric voltage between the stimulating electrodes 6, 7 and therefore ascertains imbalances of electric charges or differences in charge on the stimulating electrodes 6, 7, which are passed to a comparator 4. The comparator 4 establishes whether the voltage between the stimulating electrodes 6 and 7 ascertained by the coulombmeter or voltmeter 5 lies below, within or above a predetermined voltage range which is defined by predetermined limiting values.

The comparator 4 is connected to a charge-injector 3 which is able to generate an electric current of defined duration and intensity. The charge-injector 3 is in turn connected to the stimulating electrode 6 via an electrical line, it being possible for the connection between the charge-injector 3 and the stimulating electrode 6 to be interrupted or established by a switching contact 9. On the basis of the result ascertained by the comparator 4 with respect to the voltage between the stimulating electrodes 6 and 7, the comparator 4 transmits a corresponding signal to the charge-injector 3, whereupon the charge-injector 3 is able to apply a positive or negative electric current of defined duration and intensity to the stimulating electrode 6.

If the comparator 4 establishes that the voltage between the stimulating electrodes 6, 7 does not lie within the predetermined voltage range, the charge-injector 3 applies an appropriate electric current of defined intensity to the stimulating electrode 6 for a defined time-interval. In this case the direction of the equalising current, or the polarity of the equalising current, is chosen by the charge-injector 3 in such a way that the absolute voltage between the stimulating electrodes 6 and 7 decreases. After application of the equalising current of defined length and amplitude, the voltage can be ascertained again. If it is subsequently established by the comparator 4 that an electric voltage between the electrodes 6, 7 still lies outside the predetermined voltage range, the application of a further equalising current is repeated.

This process of alternating ascertainment of the electric voltage between the electrodes 6, 7 and the application of current pulses for the purpose of equalising imbalances of electric charges on the stimulating electrodes 6, 7 can be repeated until the electric voltage between the electrodes 6, 7 lies within the predetermined voltage range or the electric charge on the stimulating electrodes 6, 7 has been equalised. As soon as the voltage between the stimulating electrodes 6, 7 again lies within the predetermined voltage range, or the electric charge on the stimulating electrodes 6, 7 has been equalised, the charge-injector 3 no longer applies any current to the stimulating electrode 6, by, for example, the generation of current by the charge-injector 3 being switched off or by the connection between the charge-injector 3 and the stimulating electrode 6 being interrupted by the switching contact 9.

As in the case of the embodiment of the device according to the invention represented in FIG. 1, it is sufficient that the charge-injector 3 is connected to only one stimulating electrode 6, since the charge-injector 3 is capable of generating a positive or a negative voltage with the requisite current intensity in order to bring about a charge equalisation between the stimulating electrodes 6, 7. Whether a positive or a negative voltage, and which current intensity, is required for the charge equalisation between the stimulating electrodes 6, 7 is ascertained beforehand by the coulombmeter or voltmeter 5 and by the comparator 4 and passed to the charge-injector 3. By virtue of this actively controlled regulation via the coulombmeter or voltmeter 5, the comparator 4 and the closed-loop control of the equalising current by means of the charge-injector 3, it is guaranteed that the voltage between the stimulating electrodes 6 and 7 does not exceed defined limiting values, or that the electric voltage between the stimulating electrodes 6 and 7 decreases or is reduced to zero.

The device according to the invention for equalising imbalances of electric charges on the stimulating electrodes can be used generally in a system for stimulating tissue or nerves by individual or repeated stimulating pulses via stimulating electrodes and is preferably integrated within such a stimulation system. According to a particular aspect of the present invention, the device according to the invention for equalising imbalances of electric charges on the stimulating electrodes is preferably active only when no load current or no stimulating current is applied to the stimulating electrodes 6, 7 via the current source 2, i.e. if the tissue (8, 12) or nerves contacted with the stimulating electrodes (6, 7) is/are not being stimulated by stimulating pulses of the stimulating electrodes (6, 7). In this way, any possible imbalances of electric charges on the stimulating electrodes can be ascertained in particularly exact manner and equalised by almost currentless measurement.

Figure 2:
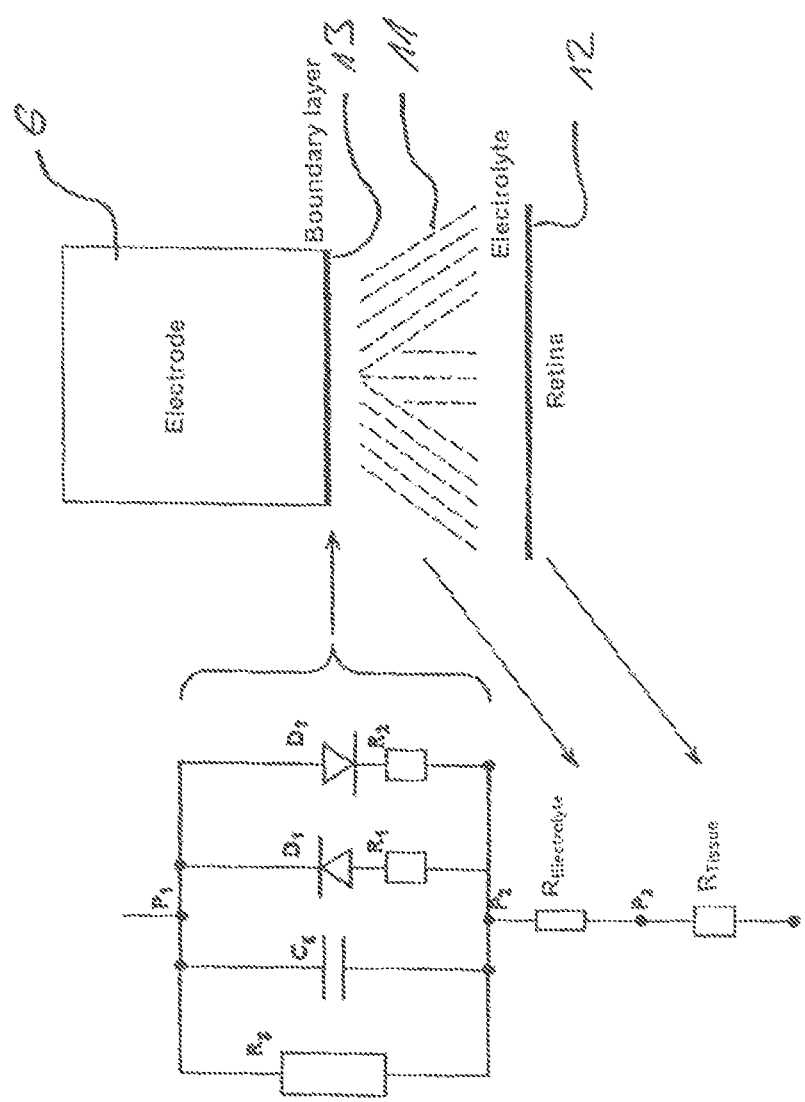
FIG. 2 shows an electrode model in the form of a schematic representation with an electrical equivalent circuit diagram for a device according to a preferred embodiment of the present invention in a stimulation system.

FIG. 2 shows an electrode model in the form of a schematic representation with an electrical equivalent circuit diagram for a device according to a preferred embodiment of the present invention for use in a stimulation system. A model for describing the fundamental processes at the stimulating electrodes of a stimulation system according to the invention is represented in FIG. 2.

The electrode model, represented in FIG. 2, of the device according to the invention will be elucidated by way of example on the basis of a retina-stimulation system for application in a human eye, wherein only one stimulating electrode 6 of the retina-stimulation system has been represented. On the right-hand side of FIG. 2 the contacting of the stimulating electrode 6 of the retina-stimulation system with the retina 12 of a human eye has been represented schematically. In this case the stimulating electrode 6 is in contact with the retina 12 of the human eye via an electrolyte 11, with a boundary layer 13 being formed between the stimulating electrode 6 and the electrolyte 11. The electrolyte 11 consists substantially of an aqueous solution in which electrically charged ions are to be found.

An electrical equivalent circuit diagram for elucidating the mode of operation of the device according to the invention is represented on the left-hand side of FIG. 2, wherein the relations of the respective structural parts of the stimulation system to the components in question of the equivalent circuit diagram have been indicated by arrows. The part of the equivalent circuit diagram that is encompassed by the brace in FIG. 2 serves for representing the fundamental processes at the boundary layer 13 between the stimulating electrode 6 and the electrolyte 11.

The equivalent circuit diagram of the boundary layer 13 between the stimulating electrode 6 and the electrolyte 11 comprises a first electrical nodal point P1, a boundary-layer resistor Rg, a capacitor Cg, a first series connection consisting of a first diode D1 and a first resistor R1, a second series connection consisting of a second diode D2 and a second resistor R2, and also a second electrical nodal point P2. The boundary-layer resistor Rg, the capacitor Cg, the first series connection consisting of the first diode D1 and the first resistor R1, the second series connection consisting of the second diode D2 and the second resistor R2 are each connected in parallel between the first electrical nodal point P1 and the second electrical nodal point P2.

The first diode D1 is connected within the first series connection in such a way that its cathode is connected to the electrical nodal point P1, whereas the second diode D2 within the second series connection is connected in such a way that its anode is connected to the electrical nodal point P1. Connected between the second electrical nodal point P2 and a third electrical nodal point P3 is an electrolyte resistance $R_{electrolyte}$, to which a specific resistance of the tissue $R_{tissue}$ is connected.

The individual components of the equivalent circuit diagram have the following physical equivalents with reference to the components of the stimulation system. The boundary-layer capacitor Cg corresponds to the electrical capacitance at the boundary layer 13 between the stimulating electrode 6 and the electrolyte 11. The boundary-layer capacitance Cg is substantially determined by the orientation of the water-dipole molecules that are present in the electrolyte 11 and also by the accumulation of the ions that are present in the electrolyte 11. During a stimulation of the retina by the stimulating electrode 6, in the course of an orderly operation of the stimulation system the ions that are present in the electrolyte are not discharged. The electrical capacitance Cg at the boundary layer is determined furthermore by the effective surface area of the electrode 6 and by the physical properties of the electrolyte 11.

The boundary-layer resistance Rg describes the behaviour of a slight transport of charge within the boundary layer 13 between the electrolyte 11 and the stimulating electrode 6. The boundary-layer resistance Rg lies within the range of 10 megohm. Transports of charge may occur within the boundary layer 13 without disadvantageous effects necessarily occurring that will be described further below.

The electrolyte resistance $R_{electrolyte}$ corresponds to the electrical resistance of the electrolyte 11 and is composed substantially of the effective surface area of the stimulating electrode 6 and the specific resistance of the electrolyte 11.

The resistance of the retina and of the subretinal tissue layers situated below it is substantially determined by the specific resistance $R_{tissue}$ of the tissue. In this case the specific tissue resistance $R_{tissue}$ is greater than the specific resistance $R_{electrolyte}$ of the electrolyte 11.

Between the electrical nodal points P1 and P2 a voltage may build up that is denoted in the following by V12. Even if the voltage between P1 and P2 does not exceed the breakdown voltages of the diodes D1 and D2, a current is able to flow within the boundary layer 13 without disadvantageous effects on the stimulating electrode 6 or on the tissue arising thereby.

The choice and the arrangement of the aforementioned electrical components of the equivalent circuit diagram indicated in FIG. 2 have been kept as simple as possible, in order to represent the fundamental processes at the boundary layer 13 between the stimulating electrode 6 and the retina 12 in readily comprehensible manner. For an exact depiction of the effects occurring in reality between the stimulating electrode 6 and the retina 12, further components would have to be added to the equivalent circuit diagram. In particular, the choice of the two diodes D1 and D2 which are arranged with opposite polarity is therefore to be understood as being merely symbolic.

In the following, disadvantageous processes will be described with reference to FIG. 2 which during the operation of a stimulation system may occur in the stimulating electrode 6, in the electrolyte 11 between the stimulating electrode 6 and the retina 12, and also at the boundary layer 13 between the electrolyte 11 and the stimulating electrode 6. In this case the diodes D1 and D2 are to be regarded as ideal elements, the breakdown voltages of which preferably lie within the range of a few tenths of a volt. In the course of operation of the stimulation system, depending on anodic or cathodic excitation of the diodes D1 and D2 as a result of the exceeding of discrete voltages between the electrical nodal points P1 and P2 over a defined period of time various effects may occur, which can essentially be differentiated into four case-specific groups:

1. The ions contained in the electrolyte 11 go into solution, and the electrode 6 dissolves.
2. The ions contained in the electrolyte 11 are discharged, and the electrode 6 grows.
3. The surface of the electrode 6 is oxidised or reduced.
4. A formation of gas occurs in the electrolyte 11.

The aforementioned effects, which in the course of operation of the stimulation system may occur in the stimulating electrode 6, in the electrolyte 11 between the stimulating electrode 6 and the retina 12, and also at the boundary layer 13 between the electrolyte 11 and the stimulating electrode 6, are disadvantageous for the stimulated tissue and for flawless functioning of the stimulation system. In connection with the drive of stimulating electrodes, it is therefore an objective to avoid the aforementioned case-specific groups of disadvantageous effects in every case. This objective is attained, on the one hand, by the voltage V12 between the electrical nodal points P1 and P2 always being kept below the breakdown voltages of the diodes D1 and D2. In order to bring this about, the various states of the stimulating electrodes have to be considered.

Figure 3:
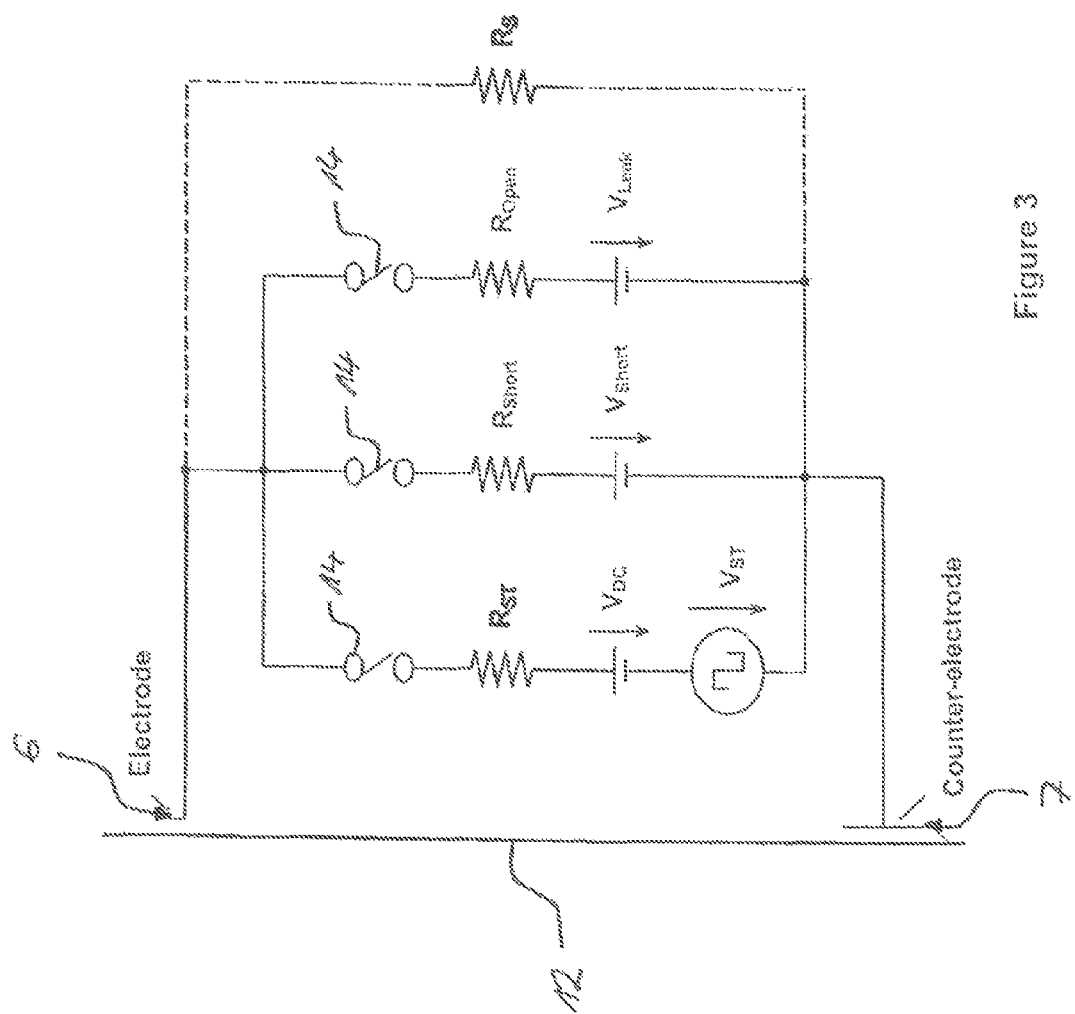
FIG. 3 shows an electrical equivalent circuit for representing varying states of the stimulating electrodes of a stimulation system with a device according to a preferred embodiment of the present invention.

FIG. 3 shows a schematic equivalent circuit for representing varying states of the stimulating electrodes of a stimulation system with a device according to a preferred embodiment of the present invention. In this representation too, a retina-stimulation system serves as an example of the use or mode of operation of the device according to the invention, with only one stimulating electrode 6 and one counter-electrode 7 of the stimulation system being represented in FIG. 3. Nevertheless, a stimulation system ordinarily includes a large number of stimulating electrodes 6, 7 which are each contacted with the retina 12 of a human eye.

The equivalent circuit diagram represented in FIG. 3 comprises several series connections arranged in parallel which each reproduce one state of the stimulating electrodes 6, 7, in which connection for the elucidation of the electrode states reference is also made to the equivalent circuit diagram represented in FIG. 2. Each of the series connections represented in FIG. 3 is connected, via one end, to the stimulating electrode 6 and, via the other end, to the stimulating electrode 7. Each of the series connections in FIG. 3 exhibits a switch 14, via which the connection of the series connection in question to the stimulating electrode 6 can be interrupted or established.

The first series connection comprises a resistor $R_{ST}$, a voltage source $V_{DC}$ and also an alternating-current source $V_{ST}$. The second series connection comprises a resistor $R_{SHORT}$ and a voltage source $V_{SHORT}$. The third series connection comprises a resistor $R_{OPEN}$ and a voltage source $V_{LEAK}$. The fourth series connection comprises a resistor $R_S$.

In the case of a mode of operation of the stimulation system without short-circuit wiring of the stimulating electrodes 6, 7 a drive frequency of approximately 60 Hz may be used as a basis, so that a stimulation cycle for the stimulating electrode 6 of approximately 16.7 ms arises. Within this stimulation cycle the stimulating electrode is stimulated over a time-interval of approximately 3 ms. The application of an electric voltage or charge to the stimulating electrodes 6, 7 in a stimulation cycle corresponds to the electrode state of the first series connection. Outside the stimulation cycle either the stimulating electrode 6 is briefly short-circuited with the counter-electrode 7, which corresponds to the electrode state of the second series connection, or the stimulating electrode is open, i.e. it does not have an electric voltage or charge applied to it, which corresponds to the electrode state of the third series connection.

Proceeding from the assumption that only approximately 10% of all the stimulating electrodes of the stimulation system are driven simultaneously, and that this drive is to some extent uniformly distributed, a stimulating electrode only has an electric voltage or charge applied to it for approximately 1.8% of the operating-time of the stimulation system. Also in the case of a non-uniform distribution of the drive of the stimulating electrodes, the time predominates in each case with about 90% of the operating-time of the stimulation system, in which the electrode is running at no load or, to be more exact, is open, i.e. does not have an electric voltage or charge applied to it.

During this time the capacitor Cg represented in FIG. 2 can be charged via the leakage current $I_{leak}$ which flows via the voltage source $V_{LEAK}$. In this case it is assumed that the resistance Rg represented in FIG. 2 amounts to approximately 10 Mohm and the voltage V12 between the electrical nodal points represented in FIG. 2 must not exceed approximately 200 mV. In order to avoid one of the aforementioned disadvantageous effects, $I_{leak}<20$ nA must hold. If the capacitor Cg is discharged in the meantime, the leakage current $I_{leak}$ may be correspondingly larger. If, on the other hand, the resistance Rg were infinitely large, $I_{leak}$ would have to be equal to 0 in order to guarantee an orderly operation of the device according to the invention.

In the course of a stimulation, a stimulating-pulse current of at most 1 mA is assumed. A deviation of 0.01% then corresponds to a direct current of 100 nA. If the electrode is stimulated for at most 10% of the time, this results in a direct current of 10 nA. This means that, without a charge equalisation between the stimulating pulses, a charge balance or a charge equalisation between the stimulating electrodes of approximately the same order of magnitude has to take place.

There is no possibility for direct measurement or monitoring of the voltage V12 between the first electrical nodal point P1 and the second electrical nodal point P2, since in the course of a measurement of the total voltage V12 the drops in voltage above the electrolyte 11 and the retinal tissue 12 are also measured. A voltage measurement or residual-potential measurement between the first electrical nodal point P1 and the second electrical nodal point P2 is therefore only possible, first of all, at times when no stimulation is taking place at the stimulating electrodes 6,7—that is to say, when measurement is being effected in virtually currentless manner.

As can be gathered from the equivalent circuit diagram represented in FIG. 3, a protective resistor $R_S$ may optionally be inserted which is connected, on one side, to the electrode 6 and, on the other side, to the counter-electrode 7; the terminals of the protective resistor $R_S$ have been represented by dashed connecting lines. This protective resistance $R_S$ may lie approximately within the range of 100 kohm and, in the event of a charge imbalance between the stimulating electrodes 6, 7 of approximately 1%, would suffice to discharge the capacitor Cg between the stimulation phases.

In addition, or alternatively, there is also the possibility of discharging the capacitor Cg between the stimulating electrodes 6, 7 by short-circuiting the electrode 6 with the counter-electrode 7. This could be effected, for example, between two stimulating pulses by means of a short circuit of the electrode 6 with the counter-electrode 7 for about 3 ms. However, in this case attention should be paid to ensuring that at this time of discharging by short-circuiting of an electrode with its counter-electrode no adjacent electrodes are stimulated that are located in the vicinity of the short-circuited stimulating electrodes.

The device may include a chip. The electrical circuits may include electronic components and also metallic conductor tracks for the contacting thereof, which may be photolithographically microstructured and accommodated on the chip.

The present invention has been elucidated through merely one application example on the basis of the electrode model and the equivalent circuit diagram in connection with a retina-stimulation system for use in a human eye. The device according to the invention that is defined by the Claims and also the process according to the invention may, of course, also be used in other stimulation systems.

The invention claimed is:

1. A device for stimulating living tissue cells or nerves, comprising:
   stimulating electrodes configured to be in contact with living nerve cells or tissue and configured to stimulate the living nerve cells or tissue by individual or repeated stimulating pulses of the stimulating electrodes;
   a pulse-generator and a current/voltage source arranged to provide the individual or repeated stimulating pulses to the stimulating electrodes, wherein the stimulating electrodes have an electric voltage and an electric charge in response to the at least one pulse;
   a coulombmeter and/or a voltmeter which is connected to the stimulating electrodes and which determines a voltage on or an imbalance of electric charges on the stimulating electrodes; and
   an electrical circuit which performs feedback control to control the electric voltage or the electric charge remaining on the stimulating electrodes as a function of the electric voltage between the stimulating electrodes and reduces or equalizes imbalances of electric charges on the stimulating electrodes; and
   wherein the electrical circuit includes a charge-injector that is connected to the current/voltage source and to the coulombmeter and/or voltmeter and to at least one of the stimulating electrodes, wherein the charge-injector generates a positive or negative electric current of defined duration and intensity based on the determination of the coulombmeter and/or voltmeter and applies the positive or negative electric current to the stimulating electrode, as a result of which imbalances of electric charges on the stimulating electrodes are reduced or equalized.

2. A device according to claim 1, wherein the pulse-generator generates electrical pulses which are amplified into the stimulating pulses by the current/voltage source and passed to at least one of the stimulating electrodes or to a number of the stimulating electrodes.

3. A device according to claim 2, wherein a shape or contour of the electrical stimulating pulses generated by the device or of current pulses for the charge equalization between the stimulating electrodes is adapted according to a type of tissue to be stimulated or to a type of nerve cells to be stimulated.

4. A device according to claim 2, further comprising a switching contact, wherein a connection of the electrical circuit to the at least one of the stimulating electrodes is configured to be interrupted or established by the switching contact.

5. A device according to claim 1, wherein the device further includes a coulombmeter and/or voltmeter which is connected to the stimulating electrodes and ascertains the electric voltage between the stimulating electrodes or ascertains imbalances at the stimulating electrodes.

6. A device according to claim 5, wherein stimulation cycles are applied to the stimulating electrodes by the electric circuit, wherein the coulombmeter and/or voltmeter ascertains the electric voltage between the stimulating electrodes between the stimulation cycles, while the tissue or nerves contacted with the stimulating electrodes is/are not being stimulated by the stimulating pulses of the stimulating electrodes, or no load current or stimulating current is being applied to the stimulating electrodes.

7. A device according to claim 1, wherein the device further includes a comparator which is connected to the charge-injector and which establishes whether the electric voltage or the differences in charge between the stimulating electrodes lies below, within or above a defined voltage range which is defined by predetermined limiting values.

8. A device according to claim 7, wherein a result ascertained by a coulombmeter and/or a voltmeter with respect to the electric voltage between the stimulating electrodes or with respect to the imbalances of electric charges on the stimulating electrodes is passed to the comparator and a result of the comparison carried out by the comparator as to whether the electric voltage or the differences in charge between the stimulating electrodes lies below, within or above a predetermined voltage range is passed to the charge-injector and on the basis of the signals passed by the comparator the charge-injector applies a positive or a negative voltage and with defined current intensity over a defined time-interval to the at least one stimulating electrode, so that the electric voltage between the stimulating electrodes or imbalances of electric charges on the stimulating electrodes are reduced or equalized.

9. A device according to claim 1, wherein the device serves for electrostimulation of a retina of an eye, as a function of incident light, with an electrical circuit preferably in the form of an integrated circuit which is designed to be implanted in the region of the retina, wherein the electrical circuit includes a number of contact-points for contacting retinal cells and a number of light-sensitive elements which drive the contact-points via the electrical circuit as a function of incident light.

10. A device according to claim 1, further comprising a chip, wherein the electrical circuit comprises electronic components and also metallic conductor tracks for the contacting thereof, which are photolithographically microstructured and accommodated on the chip.

11. A system for stimulating living tissue or nerves by individual or repeated stimulating pulses via stimulating electrodes, with a device according to claim 1, wherein the device is integrated within the stimulation system.

12. A process for operating a device for stimulating living tissue cells or nerves by individual or repeated stimulating pulses via a current/voltage source connected to stimulating electrodes, the stimulating electrodes configured to contact living nerve cells or tissue that are/is stimulated by the stimulating pulses of the stimulating electrodes, comprising the following steps:
ascertaining, by a coulombmeter and/or voltmeter of the device, an electric voltage between the stimulating electrodes or ascertaining, by the coulombmeter and/or voltmeter of the device, an imbalance of electric charges between the stimulating electrodes,
comparing the ascertained voltage between the stimulating electrodes with a predetermined voltage range,
performing feedback control with an electrical circuit that includes a charge-injector by generating and applying a positive or negative electric current of defined duration and intensity, based on the ascertained voltage or on the ascertained imbalance of electric charge, to at least one of the stimulating electrodes by means of a charge injector, as a result of which the electric voltage between the stimulating electrodes or the imbalance of electric charges remaining on the stimulating electrodes is reduced or equalized,
wherein the charge-injector is connected to the current/voltage source and to the coulombmeter and/or voltmeter and to at least one of the stimulating electrodes.

13. A process according to claim 12, further comprising:
ascertaining, by the device, the electric voltage between the stimulating electrodes also during the equalization of charge on the stimulating electrodes; and
interrupting the supply of current to the stimulating electrodes for the purpose of charge equalization as soon as the voltage between the stimulating electrodes again lies within the predetermined voltage range or no voltage is present any longer between the stimulating electrodes.

14. A process according to claim 12,
wherein stimulation cycles are applied to the stimulating electrodes,
wherein ascertaining, by the device, an electric voltage between the stimulating electrodes or ascertaining, by the device, an imbalance of electric charges between the stimulating electrodes, further comprises:
ascertaining the electric voltage between the stimulating electrodes or the imbalance of electric charges on the stimulating electrodes and/or of the equalization of charge on the stimulating electrodes between the stimulation cycles, while the tissue or nerves contacted with the stimulating electrodes is/are not being stimulated by stimulating pulses of the stimulating electrodes or no load current or stimulating current is being applied to the stimulating electrodes.

15. A process according to claim 12,
wherein ascertaining, by the device, an electric voltage between the stimulating electrodes or ascertaining, by the device, an imbalance of electric charges between the stimulating electrodes, further comprises:
ascertaining the electric voltage between the stimulating electrodes or the imbalance of electric charges on the stimulating electrodes when no stimulating current is applied to the stimulating electrodes.

16. A process according to claim 12,
wherein ascertaining, by the device, an electric voltage between the stimulating electrodes or ascertaining, by the device, an imbalance of electric charges between the stimulating electrodes, further comprises:
ascertaining the electric voltage between the stimulating electrodes or the imbalance of electric charges on the stimulating electrodes and/or of the equalization of charge on the stimulating electrodes only when no stimulating current is applied to the stimulating electrodes and to stimulating electrodes in the vicinity of the stimulating electrodes, wherein neither the stimulating electrodes nor stimulating electrodes in the vicinity of the stimulating electrodes are being stimulated by stimulating pulses.

17. A process according to claim 12, wherein the ascertainment of an electric voltage between the stimulating electrodes or of an imbalance of electric charges on the stimulating electrodes and/or of the equalization of charge on the stimulating electrodes is repeated cyclically.

18. A process according to claim 12,
wherein ascertaining, by the device, an electric voltage between the stimulating electrodes or ascertaining, by the device, an imbalance of electric charges between the stimulating electrodes, further comprises:
ascertaining the electric voltage between the stimulating electrodes or the imbalance of electric charges on the stimulating electrodes and supplying the equalizing current with defined duration and amplitude to the stimulating electrodes for the purpose of equalization of charge on the stimulating electrodes in alternating manner.

19. A system for stimulating living tissue or nerves by individual or repeated stimulating pulses via stimulating electrodes, said system comprising an electrical circuit operating by a process according to claim 12.

20. A device for stimulating living tissue cells or nerves comprising:
stimulating electrodes configured to be in contact with living nerve cells or tissue and configured to stimulate the living nerve cells or tissue by individual or repeated stimulating pulses of the stimulating electrodes;
a pulse-generator and a current/voltage source arranged to transmit the individual or repeated stimulating pulses to the stimulating electrodes, wherein the stimulating electrodes have an electric voltage and an electric charge in response to the at least one pulse;
a coulombmeter and/or a voltmeter which is connected to the stimulating electrodes; and
an electrical circuit which performs feedback control to control the electric voltage or the electric charge remaining on the stimulating electrodes as a function of the electric voltage between the stimulating electrodes and actively reduces or equalizes imbalances of electric charges on the stimulating electrodes;
wherein the device further includes a charge-injector which generates a positive or negative electric current of defined duration and intensity and applies it to the stimulating electrode to actively reduce or equalize imbalances of electric charges on the stimulating electrodes,
wherein the charge-injector is connected to the current/voltage source and to the coulombmeter and/or voltmeter and to at least one of the stimulating electrodes, wherein the stimulating electrodes comprise at least one counter-electrode.

21. A process for operating a device for stimulating living tissue cells or nerves by individual or repeated stimulating pulses via stimulating electrodes, the stimulating electrodes configured to contact living nerve cells or tissue that are/is stimulated by the stimulating pulses of the stimulating electrodes, comprising the following steps:
  ascertaining, by a coulombmeter and/or voltmeter of the device, an electric voltage between the stimulating electrodes or ascertaining, by the coulombmeter and/or voltmeter of the device, an imbalance of electric charges between the stimulating electrodes,
  comparing the ascertained voltage between the stimulating electrodes with a predetermined voltage range,
  performing feedback control with an electrical circuit that includes a charge-injector by generating and applying a positive or negative electric current of defined duration and intensity, based on the ascertained voltage or on the ascertained imbalance of electric charge, to at least one of the stimulating electrodes by means of a charge-injector to actively reduce or equalize the electric voltage between the stimulating electrodes or the imbalance of electric charges remaining on the stimulating electrodes,
  wherein the stimulating electrodes comprise at least one counter-electrode,
  wherein the charge-injector is connected to the current/voltage source and to the coulombmeter and/or voltmeter and to at least one of the stimulating electrodes.

* * * * *